United States Patent
Fehre et al.

(10) Patent No.: US 9,232,885 B2
(45) Date of Patent: *Jan. 12, 2016

(54) METHOD AND DEVICE FOR DETECTING TUMOROUS TISSUE IN THE GASTROINTESTINAL TRACT WITH THE AID OF AN ENDOCAPSULE

(75) Inventors: Jens Fehre, Hausen (DE); Ralf Nanke, Neunkirchen am Brand (DE)

(73) Assignee: Siemens Aktiengesellschaft, Munich (DE)

( * ) Notice: Subject to any disclaimer, the term of this patent is extended or adjusted under 35 U.S.C. 154(b) by 343 days.

This patent is subject to a terminal disclaimer.

(21) Appl. No.: 13/805,205

(22) PCT Filed: May 11, 2011

(86) PCT No.: PCT/EP2011/057582
§ 371 (c)(1),
(2), (4) Date: Dec. 18, 2012

(87) PCT Pub. No.: WO2011/160892
PCT Pub. Date: Dec. 29, 2011

(65) Prior Publication Data
US 2013/0096438 A1    Apr. 18, 2013

(30) Foreign Application Priority Data
Jun. 23, 2010   (DE) .......................... 10 2010 024 732

(51) Int. Cl.
*A61B 5/05*    (2006.01)
*A61B 1/04*    (2006.01)
(Continued)

(52) U.S. Cl.
CPC ................. *A61B 1/043* (2013.01); *A61B 1/041* (2013.01); *A61B 5/0059* (2013.01);
(Continued)

(58) Field of Classification Search
CPC ............. A61B 5/0059; G01N 21/6408; G01N 21/6486
See application file for complete search history.

(56) References Cited

U.S. PATENT DOCUMENTS

| | | |
|---|---|---|
| 5,562,100 A | 10/1996 | Kittrell et al. |
| 7,572,284 B2 | 8/2009 | Abraham-Fuchs et al. |

(Continued)

FOREIGN PATENT DOCUMENTS

| | | |
|---|---|---|
| CN | 101234026 | 8/2008 |
| DE | 10 2005 032 290 | 1/2007 |

(Continued)

OTHER PUBLICATIONS

Salomon et al. "The Feasibility of Prostate Cancer Detection by Triple Spectroscopy," European Urology, vol. 55 (2009) pp. 376-384.
Weiss et al., "Anomalous Protein Diffusion in Living Cells as Seen by Fluorescence Correlation Spectroscopy", Biophysical Journal, vol. 84, No. 6, 2003, pp. 4043-4052.
(Continued)

*Primary Examiner* — Joel Lamprecht
(74) *Attorney, Agent, or Firm* — Schiff Hardin LLP

(57) ABSTRACT

In a method and apparatus for detecting tumorous cell tissue in a gastrointestinal tract, electromagnetic radiation is emitted in a locally defined manner from an endoscope onto cell tissue and, after deactivation of the radiation, the decay of the inherent fluorescence intensity of the irradiated cell tissue, excited by the electromagnetic radiation, is detected, with temporal and spectral resolution and with a known scanning rate for at least one wavelength. From the intensity measurement values obtained in this manner, the difference autocorrelation function of the intensity decay is determined, from which a fractal dimension for the irradiated cell tissue is determined. The value of the fractal dimension is used to classify the irradiated cell tissue as to a degree to which the cell tissue is tumorous.

21 Claims, 5 Drawing Sheets

(51) Int. Cl.
  *A61B 5/00* (2006.01)
  *G01N 21/64* (2006.01)
  *G06K 9/00* (2006.01)

(52) U.S. Cl.
  CPC ............ *A61B 5/0071* (2013.01); *A61B 5/0075* (2013.01); *A61B 5/0084* (2013.01); *A61B 5/4205* (2013.01); *G01N 21/6408* (2013.01); *G01N 21/6486* (2013.01); *G06K 9/00147* (2013.01); *G06K 2209/053* (2013.01)

(56) References Cited

U.S. PATENT DOCUMENTS

| | | | |
|---|---|---|---|
| 8,187,166 B2 | 5/2012 | Kuth et al. | |
| 8,417,324 B2 | 4/2013 | Mycek et al. | |
| 8,981,317 B2 * | 3/2015 | Schreiber et al. | 250/458.1 |
| 2002/0150285 A1 | 10/2002 | Nelson | |
| 2005/0192478 A1 | 9/2005 | Williams et al. | |
| 2009/0270702 A1 | 10/2009 | Zeng et al. | |
| 2009/0312618 A1 | 12/2009 | Hengerer et al. | |
| 2010/0292543 A1 | 11/2010 | Levitt et al. | |
| 2012/0252057 A1 | 10/2012 | Schrelber et al. | |

FOREIGN PATENT DOCUMENTS

| | | |
|---|---|---|
| DE | 10 2006 014 857 | 7/2007 |
| EP | 2 251 675 A1 | 11/2010 |
| WO | 2006001020 A2 | 1/2006 |
| WO | WO 2006/001020 | 1/2006 |
| WO | WO 2010/130254 | 11/2010 |

OTHER PUBLICATIONS

Salomon et al., "Prostate cancer detection by laser induced autofluorescence and multicomponent spectroscopy", Proceedings of SPIE—The International Society for Optical Engineering—International Conference on Lasers, Applications, and Technologies 2007: Laser Technologies for Medicine 2007 SPIE US, vol. 6734.

Benda et al., "TCSPC upgrade of a confocal FCS microscope", Review of Scientific Instruments, vol. 76, No. 3, 2005, pp. 033106-1-033106-4.

Petersen et al., "Quantitation of Membrane Receptor Distributions by Image Correlation Spectroscopy: Concept and Application", Biophysical Journal, vol. 65, Sep. 1993, pp. 1135-1146.

"Optical Cancer Diagnostics by Cooperative Phenomena," Gerich et al., Joint Korean-German Symposium on Medical Diagnostics (Oct. 29, 2009).

"Endomikroskopie ermöglicht gezielte Biopsien", Ärzte Zeitung Verlags-GmbH, Ärzte Zeitung, Nov. 25, 2004.

Gerich et al: "Detection of Cancer-Cells in Prostate Tissue with Time-Resolved Fluorescence" Frauenhofer IZFP.

Mini-Spectrometers—Compact and low cost mini-spectrometers, Hamamatsu Photonics K.K., Solid State Division, www.hamamatsu.com Oct. 2009.

Petersen et al: Quantitation of membrane receptor distributions by image correlation spectroscopy: concept and application, Biophysical Journal, New York, US, US, Bd. 65, NR.3, Sep. 1, 1993, pp. 1135-1146.

"Fluoreszenzdiagnostik in der Gastroenterologie", http://www.qualimedic.de/autofluoreszenzendoskopie.html, Apr. 14, 2010.

* cited by examiner

METHOD AND DEVICE FOR DETECTING TUMOROUS TISSUE IN THE GASTROINTESTINAL TRACT WITH THE AID OF AN ENDOCAPSULE

BACKGROUND OF THE INVENTION

1. Field of the Invention

The invention concerns a method to detect tumorous cell tissue in the gastrointestinal tract with the use of an endocapsule.

To detect carcinomas of the gastrointestinal tract—for example in the course of a stomach endoscopy—tissue samples are extracted and examined for the presence of a carcinoma. A number of biopsies are frequently required. In order to reduce their number, a procedure known as autofluorescence endoscopy is used in which the fluorescence of substances inherent to the body is utilized, which substances occur in an increased concentration in malignant tissue due to increased metabolic activity. An additional possibility for biopsy control is the application of endomicroscopy, i.e. an examination with the aid of a microscope integrated into an endoscope, wherein a contrast agent must be administered to the patient to stain the tissue. However, biopsies continue to be necessary in both cases.

The extracted tissue samples are histologically examined in a laboratory. For example, slices are produced from the deep-frozen tell tissue samples, which slices are then assessed by the pathologist. A high time cost is necessary for this since not only the sample preparation, but rather also the documentation and the transport require time. Wait times also cannot be avoided. The results are often only present a few days later, which leads to a large psychological stress for the respective patient.

In addition to the aforementioned assessment of tissue samples, it is also known to conduct a fluorescence cystoscopy for a tumor diagnosis. Tumorous cell tissue is thereby made light-sensitive with suitable chemical substances, and fluorescence at the cells prepared in such a manner is excited upon exposure with light. The light for excitation has a different color than the fluorescence light. However, the substances that are used are strongly phototoxic and can cause necrosis at the correspondingly treated tissue. This can also be utilized for a therapy against carcinomatous tumors, but the knowledge of the positions and the propagation of tumorous cell tissue is required.

A technique known as 5-ALA induced detection (in which 5-aminolevulinic acid is injected), or methods that are commercially known as Hexvix and TOOKAD and in which other photoactive substances are used, are used to detect tumorous cell tissue.

It is disadvantageous that substances that are stressful to the respective patient immediately (but also subsequently over a longer time period) must be introduced into the body of the patient. After the injection of the substances, the examinations cannot be implemented immediately afterward since a reaction time (that can vary from patient to patient) must elapse.

A method for a laser-induced fluorescence of tissue is moreover known from DE 689 25 586 T2, in which method it should be possible to conclude the respective cell tissue type via a fluorescence excitation and the detection of specific characteristic wavelengths in the detected wavelength spectrum of the fluorescence light.

However, it has been shown that the inherent fluorescence of the body's own chromophores that can be excited to fluorescence in cell tissue (that can be tumorous or healthy) using the occurrence of a wavelength (or possibly also multiple wavelengths) that occur in the fluorescence light spectrum is not unambiguous since a cooperative response of the examined cells cannot be disregarded. These different factors and the biomolecular cell structure have a strong influence, and an association as to whether it is healthy or tumorous cell tissue is not possible with sufficient certainty.

SUMMARY OF THE INVENTION

An object of the invention is to achieve a detection of tumorous cell tissue in the gastrointestinal tract of a subject in the course of a capsule endoscopy in a shorter amount of time, and with sufficient finding certainty.

In accordance with the invention, with the use of a radiation source present in an endocapsule, locally defined electromagnetic radiation is emitted toward the cell tissue of the gastrointestinal tract that is to be examined (for example the stomach mucosa), and after a deactivation of the radiation source at the time $t_0$, the decay response of the inherent fluorescence intensity of the cell tissue that is excited by the electromagnetic radiation is detected with temporal and spatial resolution. The detection of the inherent fluorescence intensity takes place with one or more known sample rate(s) and is implemented for at least one wavelength. The sample rate is preferably kept constant during the detection.

With the determined intensity measurement values, the difference autocorrelation function C(t) of the intensity decay response is determined according to Equations (1) and (2), under consideration of the respective known sample rate(s).

$$I(t)=I(t_0)-[I(t_0)-I(t\rightarrow\infty)]*[1-R(t-t_0)] \quad (1)$$

with $$R(t-t_0)=<\Delta I(t)\Delta I(t_0)>_t<\Delta I^2>_t \text{ and } \Delta I(t)=I(t)-I(t\rightarrow\infty) \quad (2)$$

$I(t\rightarrow\infty)$ is the excited fluorescence light after an infinitely long relaxation that is very small. The relaxation function R(t) results from the correlation function of the fluorescence fluctuations, wherein $< >_t$ represents the temporal mean.

The function C(t)=2[1−R(t)] represents the associated difference correlation function for which the following response can be taken into account given cooperative fluorescence processes:

$$C(t)\sim t^{2H} \quad (3)$$

The exponent H, or the fractal dimension of the stochastic intensity fluctuations $D_F$ that can be calculated from this, is a characteristic value for the assessment.

$D_F$=2−H results and can be used to differentiate healthy and tumorous cell tissue. The exponent H can be determined via linear regression.

The value $D_F$ can be used for a classification with regard to a tumor affliction of the respective exposed cell tissue.

A comparison with a tumor-specific threshold can be implemented for the classification. However, a specification of a probability of a presence of a tumor can also take place in the classification.

Under consideration of the specified Equations, the fractal dimension $D_F$ is calculated for the respective exposed cell tissue and the value of the determined fractal dimension $D_F$ can then be compared with a tumor-specific threshold. Upon exceeding the threshold, the exposed cell tissue of the cell tissue sample is classified as tumorous. Given a shortfall of this threshold, the cell tissue is healthy. The threshold is a numerical value between 1 and 2.

An exposure, detection and calculation of the fractal dimension $D_F$ can thus be implemented at the examined cell tissue in vivo in order to localize healthy tissue and possible tumorous cell tissue. A finding can take place at different positions in that the endocapsule is moved, guided by magnets, to the respective positions. For this an endocapsule includes a magnet system which interacts with an external magnetic field, for example as described in DE 10142253 C1.

In the evaluation of the intensity decay response, collective electron transitions in cell tissue are described in the invention via an algebraic time response.

It is preferable to use monochromatic electromagnetic radiation for the inherent fluorescence excitation of the exposed cell tissue. Electromagnetic radiation in the wavelength range between 200 nm and 650 nm are particularly suitable here. Laser light sources can be used as a radiation source. Electromagnetic radiation with a wavelength of 337 nm has proven to be advantageous for the excitation of the inherent fluorescence.

As already noted, only a selected wavelength is detected from the spectrum of the inherent fluorescence of the cell tissue to be examined and then taken into account. However, two or more wavelengths that deviate from one another and then can be markedly larger or smaller in relation to one another can also be taken into account.

However, it is advantageous to detect intensity measurement values within an interval around a wavelength of the excited inherent fluorescence, and to determine the difference autocorrelation function of the intensity decay response C(t) of the mean values that have been calculated from the fluorescence intensities detected at the same time for the different wavelengths within the wavelength interval, and to calculate from these the fractal dimension $D_F$ for the exposed cell tissue.

At least 30 wavelengths from the selected wavelength interval should be considered for the mean calculation. The difference of the spacings of the wavelengths from this wavelength interval that are thereby considered should be respectively of equal size. For example, the detection can thus be implemented within a wavelength interval of 421 nm±15 nm.

The detection can be implemented with a spectrometer at a sample rate ≤1000 ps, preferably ≤100 ps, particularly preferably at approximately 50 ps.

Examinations of cell tissue can be implemented at multiple positions. However, a respective identical exposure of the selected positions of the cell tissue should thereby be maintained. A respective identically large area should thus be exposed with the same respective energy. For this purpose, the spacing of one or more optical fibers from the surface of the cell tissue that is to be exposed should be constant. For an evaluation and possible consideration in an immediately following operative procedure on a patient (or an operative procedure that is to be implemented later) in which the examination has been implemented in vivo, the knowledge of the respective position at the cell tissue is thus to be detected and documented so that it can be reproduced.

The examinations of cell tissue can be implemented successively or simultaneously at multiple positions. In the latter cited case, electromagnetic radiation can, for example, be directed—through multiple, correspondingly arranged optical fibers—toward cell tissue or the cell tissue sample at various locations to excite the inherent fluorescence, and after the deactivation of the radiation source the intensity I(t) of the electromagnetic radiation emitted from the cell tissue as a result of the inherent fluorescence of the cell tissue are then directed via optical fibers to a detector.

With the invention, an examination can be implemented promptly and directly in an operating room. The possibility exists to differentiate tumorous cell tissue from healthy cell tissue with very high probability. With knowledge of the respective extraction location, the invention offers a good basis for decision as to where and how much cell tissue should be operatively removed.

A device that includes an endocapsule for implementation of the method according to the invention is designed so that living cell tissue, defined locally, is charged with electromagnetic radiation emitted from a radiation source, and a detector for temporally and spectrally resolved detection of the inherent fluorescence intensity of the respective previously exposed cell tissue is connected to an electronic evaluation unit with which the different autocorrelation function C(t) can be determined from the determined intensity measurement values. With the electronic evaluation unit, the fractal dimension $D_F$ can be calculated and this value of the fractal dimension $D_F$ can be compared with a tumor-specific threshold. An endocapsule can thereby include all required components or only parts of these, as is explained in detail further below.

A time-consuming preparation of the cell tissue to be examined as it is required in a biopsy is omitted. The physical stress of patients can thereby be reduced since the examination result is present in a markedly shorter amount of time. A very good differentiation can be made between malignant and benign cell tissue.

No injection of additional substances into the body of patients (with the aforementioned disadvantages) is required either.

DESCRIPTION OF THE PREFERRED EMBODIMENTS

Figure 1:
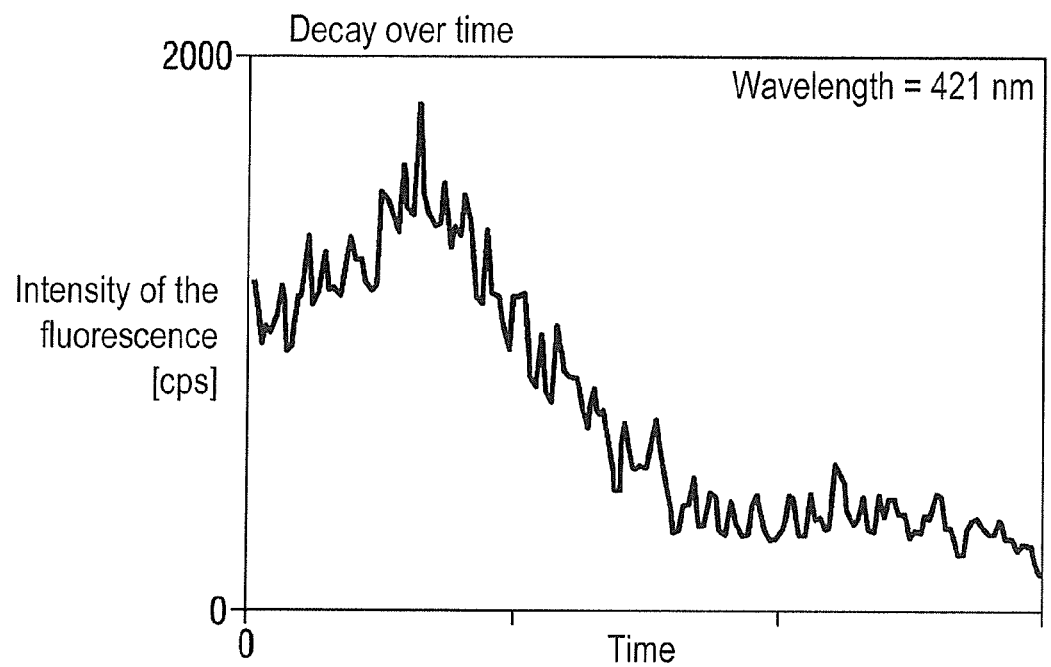
FIG. 1 is a diagram of the intensity decay response given a constant wavelength of 421 nm, acquired with temporal resolution.
Figure 2:
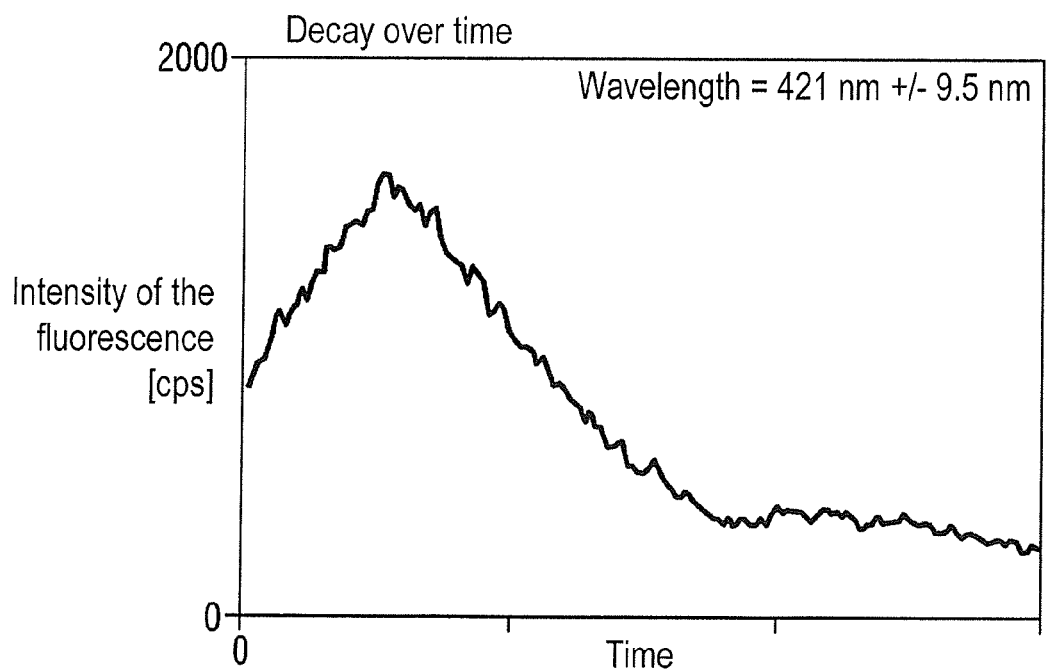
FIG. 2 is a diagram of the intensity decay response acquired with temporal resolution, created with the mean value of multiple wavelengths within a wavelength interval around the wavelength of 421 nm.
Figure 3:
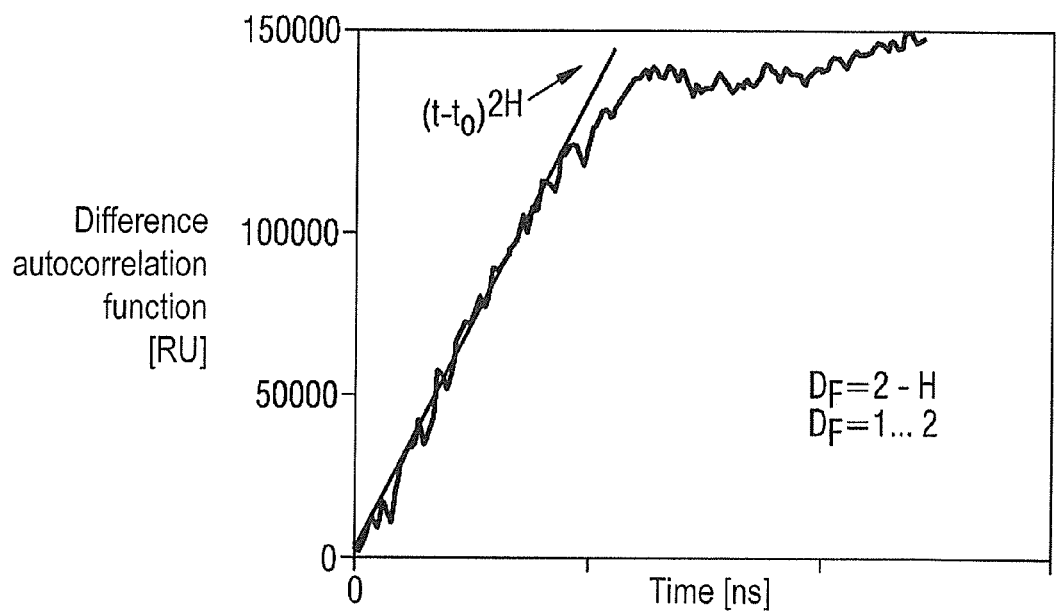
FIG. 3 shows the curve of the difference autocorrelation function over time during decay of the intensity.

The diagrams In FIGS. 1 through 3 are based on examinations that were conducted not in vivo but rather in vitro for reasons of simplification, and for reasons of reproducibility. The cell tissue samples were laid in a groove that represented a receptacle of the cell tissue samples and directed electromagnetic radiation via an optical fiber to specific, predetermined positions of the cell tissue samples. A nitrogen laser was used as a radiation source. The electromagnetic radiation used for the inherent fluorescence excitation of the cell tissue had a wavelength of 337 nm.

The extracted cell samples were cooled to a temperature of 15° C. to slow necrosis and held at this temperature at least until the end of the examination.

After deactivation of the radiation source at $t_0$, the electromagnetic radiation emitted from the cell tissue as a result of the inherent fluorescence was directed via the same optical fiber to a spectrometer with which a detection in the wavelength interval from approximately 300 nm to approximately 600 nm was possible.

A characteristic wavelength of 421 nm has been selected at which increased intensities of the inherent fluorescence occurred.

In the detection, a sampling rate of 50 ps was maintained and a detection of the intensity was made from the point in time $t_0$ over a time period of 10 ns. An evaluation according to Equations (1) through (3) was made with the intensity measurement values, and the difference autocorrelation function was determined, as shown in FIG. 3.

Since a noise was to be recorded at the decay response of the intensity of an individual wavelength, the evaluation was repeated with calculated mean values in analog form. Intensity values were thereby used within a wavelength interval of 421 nm±9.5 nm. FIG. 2 shows the intensity decay response that is thus determined. The mean value calculation thereby took place from 60 wavelengths from this wavelength interval, which 60 wavelengths respectively have a difference of 0.315 nm relative to one another.

As arises from the diagram shown in FIG. 3, the value of the fractal dimension $D_F$ can be determined with the defined difference autocorrelation function and the slope of a straight line with $(t-t_0)^{2H}$ and given knowledge of the exponent H.

The determined value $D_F$ can be compared with a tumor-specific threshold for the respective examined position of the respective cell tissue sample. For the examined tumors, this threshold was between 1.31 and 1.32.

However, if the determined value $D_F$ is below the threshold, it can be assumed that the examined cell tissue in the respective cell tissue sample is healthy cell tissue free of tumor cells, at least at the location of the sample at which the examination has been conducted.

However, the invention can also be implemented at gleast two elements that can be detectable with the spectrometer, which wavelengths have a larger interval from one another. For example, the temporal intensity decay response can be implemented at the wavelengths 370 nm and 430 nm, possibly also with a described mean value calculation.

A device with which an examination (of the stomach mucosa 1, for example) can be made in the manner described above is either formed by an endocapsule 2 that includes all necessary mechanisms or comprises an endocapsule in which only a portion of the necessary mechanisms (but in all cases a radiation source) are included, wherein the remaining portion of the mechanisms are located outside of the endocapsule and outside of the patient body (see FIG. 4-10).

Figure 4:
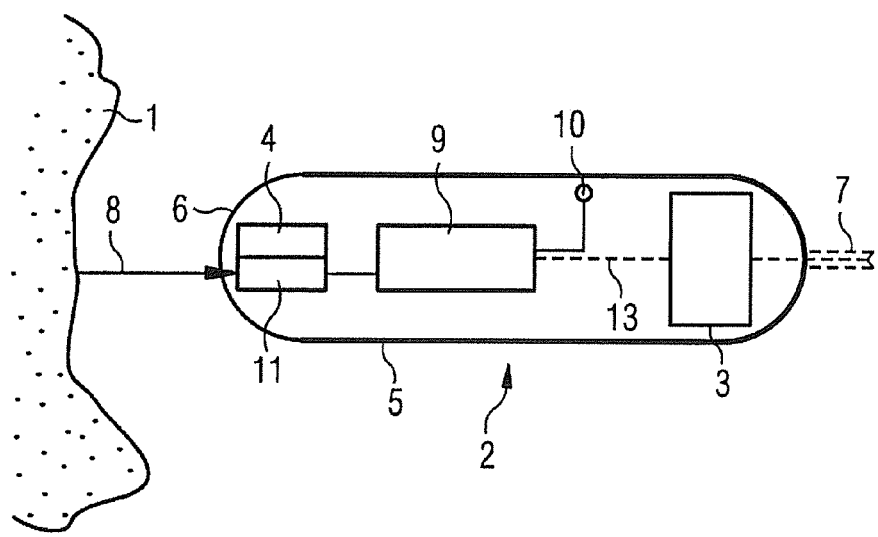
FIGS. 4-10 respectively show devices or endocapsules of different embodiments in accordance with the presence invention.

A magnet system 3 that serves for navigation of the endocapsule with the use of an external magnetic field is present in the inner space of an endoscopy 2. For fluorescence excitation of cell tissue (for example the stomach mucosa 1), the endocapsule 2 includes a radiation source 4, for instance in the form of a laser diode or an LED (FIG. 4). The housing 5 of the endocapsule 2 is penetrated by an opening or, respectively, a window 6 made of radiation-permeable material in the region of the radiation source 4. The window 6 is arranged at one end of the endocapsule 2, for example. A battery (not shown) can be present in the endocapsule 2 to supply power to the radiation source 4. Alternatively, the power supply can take place via a battery or other power source arranged outside of the body, which battery or other power source is connected via a connecting cable 7 with the radiation source 4. To detect the inherent fluorescence of the examined cell tissue, a detector 11 to detect the fluorescence radiation 8 of the cell tissue is present in the region of the window 8. For example, the detector can be formed from one or more photodiodes as well as a lens and filter system (not shown), wherein the latter serves for spectral resolution of the inherent fluorescence. For example, a mini-spectrometer that already includes an optical system for spectral resolution can serve as a detector 11. For example, the spectrometers CM10988MA and CM11009MA that are available from Hamamatsu Deutschland GmbH are suitable. The detector 11 detects the inherent fluorescence intensity of the cell tissue spectrally and with temporal resolution and relays the corresponding data to an electronic evaluation unit 9 which is arranged within the endocapsule 2, corresponding to FIGS. 4 and 5. The data calculated by the evaluation unit 9, which data allow a conclusion about the presence or non-presence of a tumor, are transmitted to a device present outside of the patient body either via a radio interface 10 present in the endocapsule 2 or with a signal line 13 (for example via the connecting cable 7). For example, the device comprises a monitor on which a color coding or numerical values for the tumor probability are presented.

Figure 5:
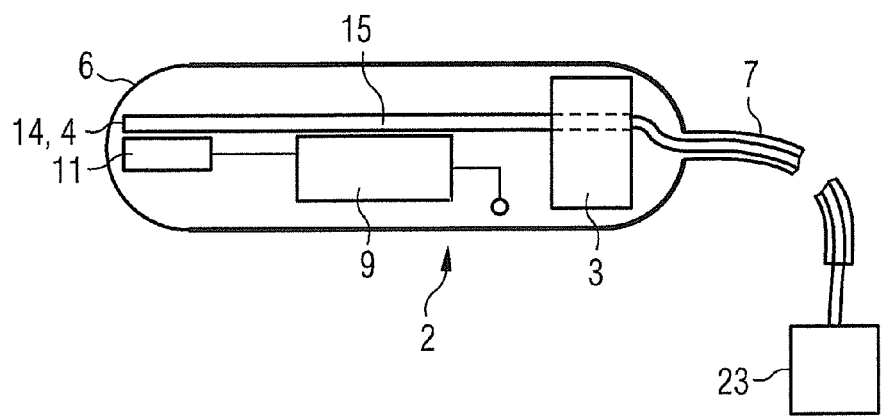

In the endocapsule 2 shown in FIG. 5, the radiation source is formed by the light exit window 14 of an end of an optical waveguide 15 arranged within the endocapsule 2. The optical waveguide 15 is directed out of the patient body via a connecting cable 7 connected with the endocapsule 2, wherein electromagnetic radiation is fed into the other end of the optical waveguide with the aid of an external radiation source 23.

Figure 6:
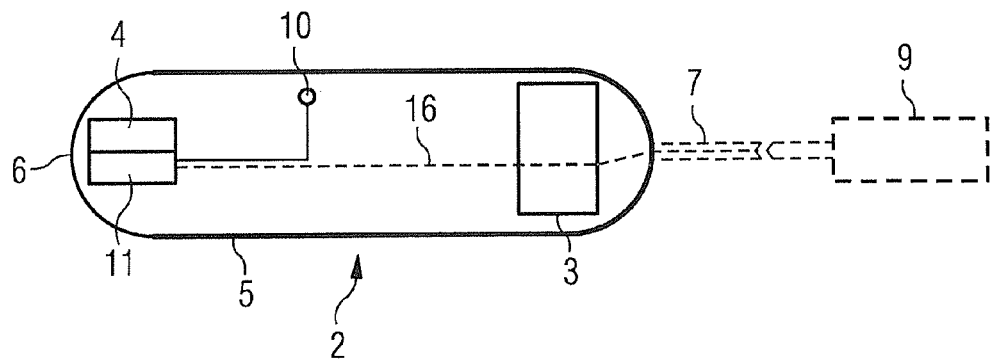

In the endocapsule 2 shown in FIG. 6, the electronic evaluation unit 9 is located outside of the endocapsule 2 and also outside of the patient body. The raw data detected by the detector 11 are transmitted to the external evaluation unit 9 either via a radio interface 10 or via a signal line 16. The signal line 16 can run in a connecting cable 7 fixed to the endocapsule 2, wherein this connecting cable 7 can include other additional supply lines, for instance for power supply of the radiation source 4. However, the radiation emission can also take place via the exit window 14 of an optical waveguide, as in the exemplary embodiment shown in FIG. 5.

Figure 7:
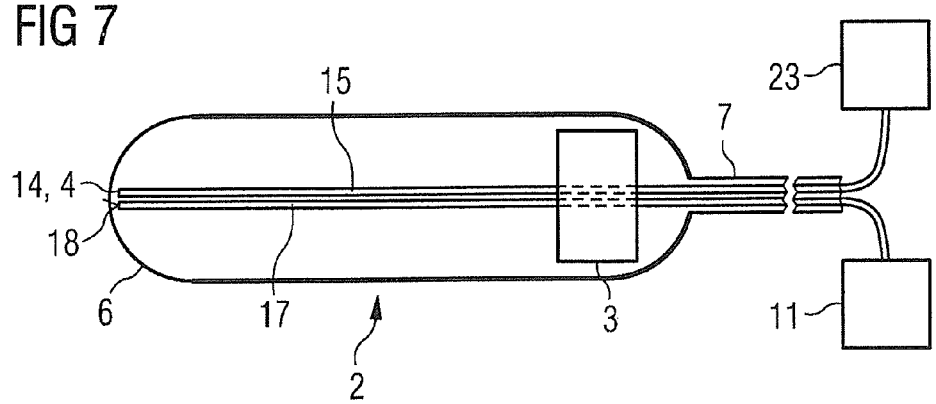
Figure 8:
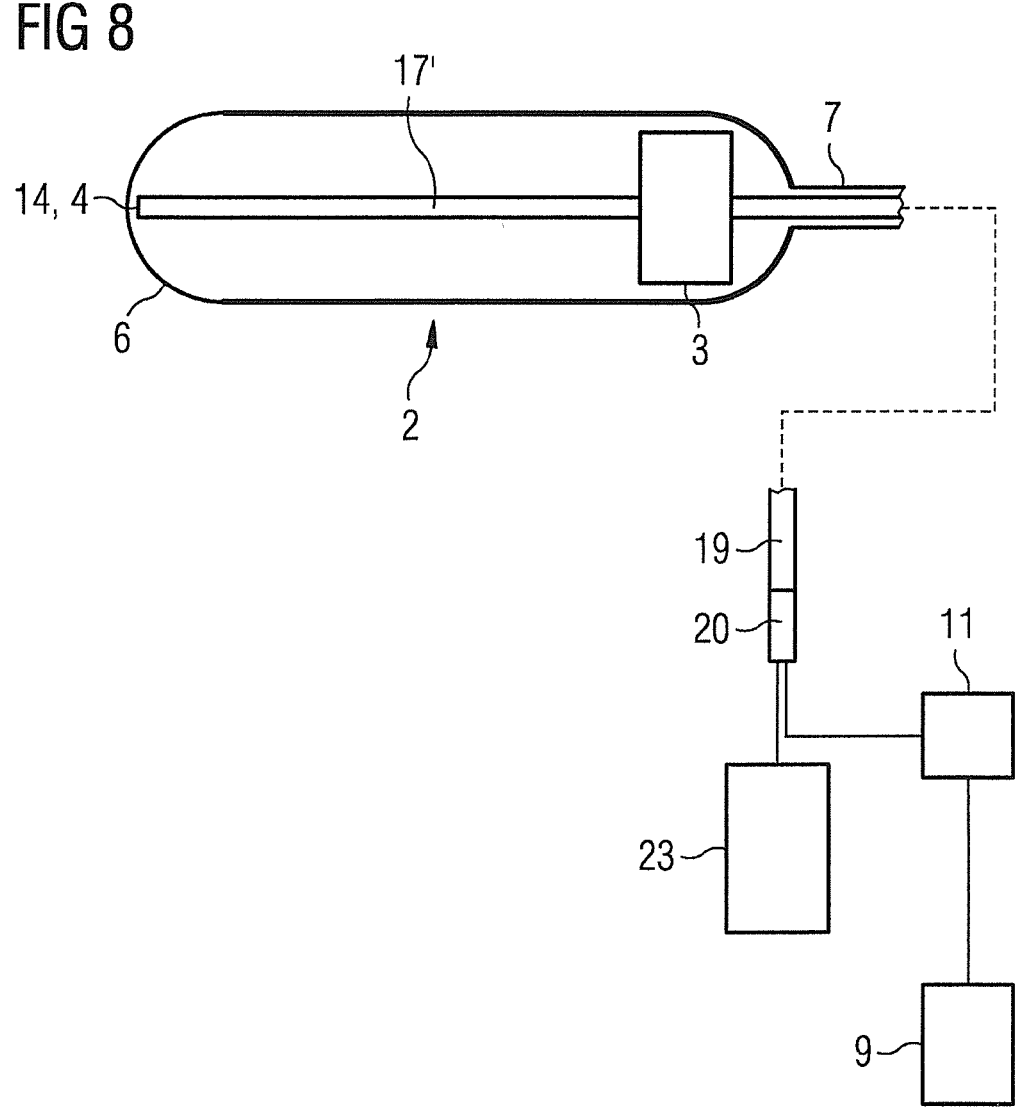
Figure 9:
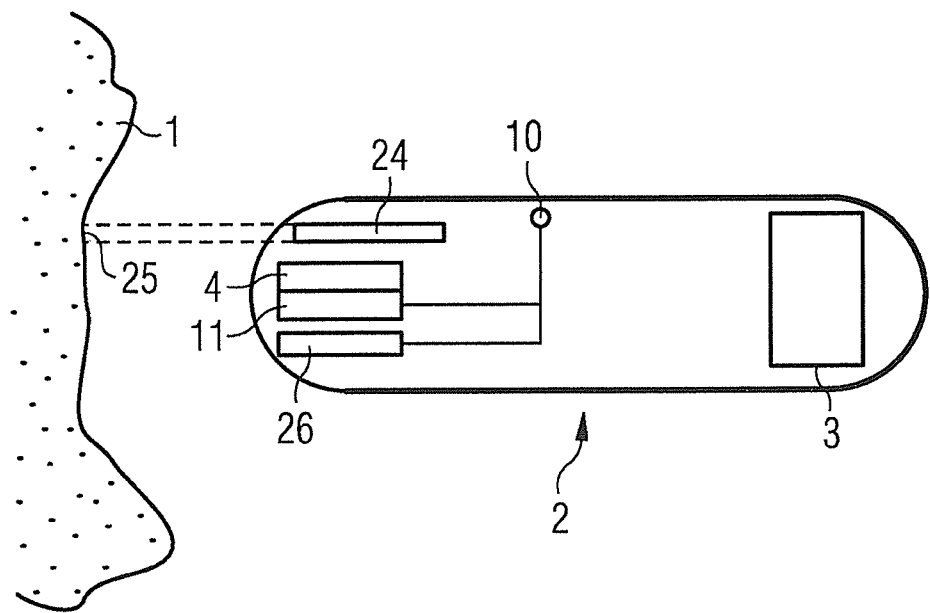
Figure 10:
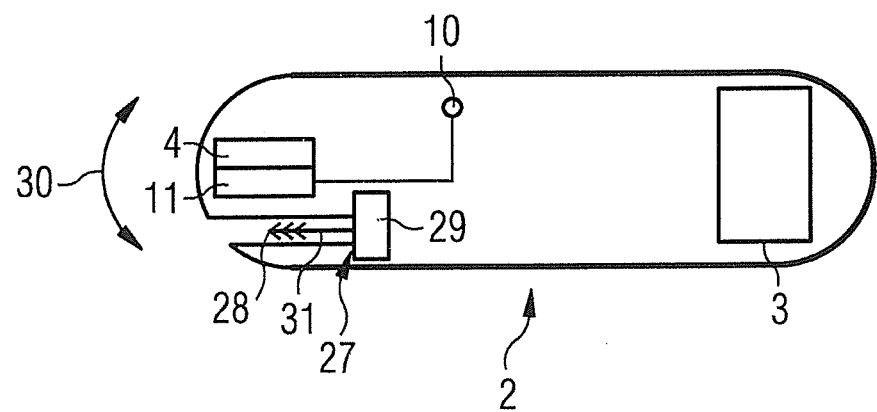

An additional structural simplification, and therefore also a shrinking of the endocapsule 2, is achieved if the detector 11 is also arranged outside of the patient body (FIG. 7). Only an optical waveguide 17 that ends in the region of the window 6 is present in the endocapsule 2, wherein the inherent fluorescence radiation arrives in the optical waveguide 17 via the face 18 of said optical waveguide 17. The radiation source 4 can be formed by a module and an LED or a laser diode, or by an optical waveguide 15 or by its light exit window 14. An additional simplification of the endocapsule 2 can take place in that an optical waveguide serving for excitation of the cell tissue and an optical waveguide serving to detect the inherent fluorescence are formed by a single optical waveguide 17' (FIG. 8). Its end arranged outside of the patient body can be associated with a beam splitter 20. With this the electromagnetic radiation of an external radiation source 23 (thus a radiation source 23 that is arranged outside of the patient body) for the excitation of the inherent fluorescence can be directed via the optical waveguide to the cell tissue, wherein after the deactivation of the radiation source 23 the inherent fluorescence radiation is introduced via the optical waveguide 17' into the detector 11, and its data are transmitted to the evaluation unit 9. The optical waveguide 17' as well as the additional aforementioned optical waveguide 15 and 17 can be formed by one or multiple optical fibers. The optical waveguides are advantageously provided with a protective jacket (not shown) or travel within a connecting cable 7 fixed to the endocapsule 2.

In all embodiment variants of an endocapsule 2 that are described above, a laser light source 24 operating in the visible range can be present in this. A measurement spot 25 is generated on the examined cell tissue with this laser light source 24. Furthermore, a camera 26 is present in the endocapsule 2, such that the measurement spot is visible at the images of the examined tissue and its surroundings that are acquired with the camera and, for example, allows an orientation over the examined area. During the detection of the inherent fluorescence radiation, the distance between the detector 11 and the surface of the examined cell tissue should not change significantly or, respectively, a change of the distance should be accordingly taken into account and corrected in the evaluation. This is done with a distance measurement device described in DE 10 2006 014 857 A1 that—in addition to the laser light source 24 and the camera 26—comprises an evaluation unit (not shown) that can be integrated into the evaluation unit 9, for example. The light beam generated by the laser light source generates a distance-independent light marker or, respectively, the measurement spot 25 on the cell tissue. The shape and size of the measurement spot 25 that is transmitted out from the camera 26 (for instance via the radio interface 10) is thereby analyzed by the evaluation unit (not shown) with the aid of an image processing software, and the respective distance of the endocapsule 2 or, respectively, of the detector 11 from the cell tissue is determined from the shape and/or size of the measurement spot 25. A distance varying during the measurement can thus be compensated accordingly by the evaluation unit 9 in the calculation of the fractal dimension $D_F$. The images acquired by the camera 26 are transmitted out via cable or via radio interface 10.

A fixed distance of the detector 11 from the cell tissue can be achieved in that a fixing device 27 is present in the endocapsule 2, with which fixing device 27 this endocapsule 2 can be anchored in the tissue of the gastrointestinal tract. Such a fixing device 27 is described in DE 10 2005 032 290 A1. It comprises an anchor 28 that can be released via a driver device 29 and is connected with the endocapsule 2 via a thread 31. The anchor 28, for example, can be found of a material that dissolves after a certain time. In the case of an endocapsule 2 equipped with a fixing device 27, as well as in other cases, it can be advantageous if radiation source 4 and detector 11 are arranged so as to be spatially variable (for instance are pivotable) within the endocapsule 2, as this is indicated by the double arrow 30 in FIG. 10.

Although modifications and changes may be suggested by those skilled in the art, it is the intention of the inventors to embody within the patent warranted heron all changes and modifications as reasonably and properly come within the scope of their contribution to the art.

The invention claimed is:

1. A method to detect tumorous cell tissue in a gastrointestinal tract of a subject comprising:
    introducing an endocapsule into the gastrointestinal tract of the subject and, from said endocapsule in the gastrointestinal tract, emitting locally defined electromagnetic radiation toward solid tissue in the gastrointestinal tract, and thereafter deactivating said electromagnetic radiation, and thereby producing a decay of inherent fluorescence intensity as a response of said cell tissue excited by said electromagnetic radiation, and detecting intensity measurement values that occur during said decay of inherent fluorescent intensity;
    communicating the detected intensity measurement values to a computerized processor and, in said computerized processor automatically determining a difference autocorrelation function of the decay response of the inherent fluorescent intensity from said detected intensity measurement values;
    in said processor, automatically calculating, from said difference autocorrelation function, fractal dimension for the cell tissue irradiated with said electromagnetic radiation; and
    making a value of the determined fractal dimension available as an electronic signal at an output of said computerized processor in a form allowing a classification to be made as to a degree to which said cell tissue that was irradiated with said electromagnetic radiation is tumorous.

2. A method as claimed in claim 1 comprising irradiating said cell tissue with monochromatic electromagnetic radiation to excite said inherent fluorescence intensity of said cell tissue.

3. A method as claimed in claim 1 comprising detecting said intensity measurement values within an interval around a wavelength of the excited inherent fluorescence, and calculating said difference out of correlation function from mean values calculated from the fluorescence intensities detected at a same time for respectively different wavelengths within the wavelength interval.

4. A method as claimed in claim 1 comprising implementing said detecting at a constant sampling rate.

5. A method as claimed in claim 1 comprising detecting said inherent fluorescence intensity with a spectrometer at a sampling rate greater than or equal to 1000 samples per second.

6. A method as claimed in claim 1 comprising irradiating said cell tissue with monochromatic radiation at a wavelength of 337 nm to excite said inherentfluorescence, and detecting said inherent fluorescence within a wavelength interval of 421.7±15 nm.

7. A method as claimed in claim 1 comprising detecting intensity measurement values within an interval around a wavelength of the excited inherent fluorescence, and calculating said difference autocorrelation function from mean values calculated from the fluorescence intensities detected at a same time for respectively different wavelengths within the wavelength interval, and calculating said mean values for at least 30 wavelength in said wavelength interval.

8. A method as claimed in claim 1 comprising directing said electromagnetic radiation at said cell tissue from said endoscope via at least one optical fiber and detecting said intensity measurement values from light produced by said inherent fluorescence decay conducted via said at least one optical fiber.

9. A method as claimed in claim 1 comprising in said computerized processor or in a separate computerized processor, implementing an automatic classification of said degree to which said cell tissue is tumorous by implementing a comparison with a tumor-specific threshold.

10. A method as claimed in claim 1 comprising in said computerized processor or in a separate computerized processor, implementing an automatic classification of said degree to which said cell tissue is tumorous by specifying a probability of a presence of a tumor.

11. An apparatus to detect tumorous cell tissue in a gastrointestinal tract of a subject comprising:
    an endocapsule configured for introduction into the gastrointestinal tract of the subject and comprising a radiation source that emits locally defined electromagnetic radiation toward solid tissue in the gastrointestinal tract, and that thereafter deactivates said electromagnetic radiation, and thereby producing a decay of inherent fluorescence intensity as a response of said cell tissue excited by said electromagnetic radiation;

a detector configured to detect intensity measurement values that occur during the decay of said inherent fluorescence intensity and to emit electrical signals corresponding to the detected intensity measurement values;

computerized evaluation unit in communication with said detector to receive electrical signals corresponding to said intensity measurement values from said detector, said computerized evaluation unit being configured to automatically determine a difference autocorrelation function of the decay response of the inherent fluorescent intensity from said intensity measurement values;

in said evaluation unit being configured to automatically calculate, from said difference autocorrelation function, fractal dimension for the cell tissue irradiated with said electromagnetic radiation; and said evaluation unit being configured to make a value of the determined fractal dimension available as an electronic signal at an output of said computerized evaluation unit in a form allowing a classification to be made as to a degree to which said cell tissue that was irradiated with said electromagnetic radiation is tumorous.

12. An apparatus as claimed in claim 11 wherein said radiation source comprises a light exit window at an end of an optical waveguide located within said endocapsule, said optical waveguide having an opposite end configured to be fed with said electromagnetic radiation from an extracorporeal radiation source.

13. An apparatus as claimed in claim 11 wherein said detector is contained within said endocapsule.

14. An apparatus as claimed in claim 11 wherein said detector is located outside of said endocapsule, and wherein said apparatus comprises an optical waveguide that transmits light produced by said inherent fluorescence of said cell tissue to said detector.

15. An apparatus as claimed in claim 14 wherein said optical waveguide communicates with a light exit window of said endocapsule, and also forms said radiation source.

16. An apparatus as claimed in claim 15 wherein said computerized evaluation unit is located outside of said endocapsule, and wherein said computerized evaluation unit and said detector are configured for signaling communication with each other.

17. An apparatus as claimed in claim 16 wherein said computerized evaluation unit and said detector are configured for wireless communication with each other.

18. An apparatus as claimed in claim 11 wherein said endocapsule contains a light source operating in the visible range, as said radiation source, and a camera operating as said detector.

19. An apparatus as claimed in claim 11 wherein said endocapsule contains a distance measurement device.

20. An apparatus as claimed in claim 11 wherein said endocapsule comprises a fixing device that anchors said endocapsule at tissue in said gastrointestinal tract.

21. An apparatus as claimed in claim 11 wherein said endocapsule comprises a mount for at least one of said detector and said radiation source, as a mounted component, and wherein said mount is configured to move said mounted component within said endocapsule to vary at least one of a location and a direction of emission of said electromagnetic radiation and detection of said inherent fluorescence of said cell tissue.

* * * * *